United States Patent

Takemura et al.

(10) Patent No.: US 10,047,043 B2
(45) Date of Patent: Aug. 14, 2018

(54) THIOL COMPOUND COMPOSITION FOR OPTICAL MATERIAL

(71) Applicant: MITSUBISHI GAS CHEMICAL COMPANY, INC., Tokyo (JP)

(72) Inventors: Kouhei Takemura, Osaka (JP); Takashi Aoki, Osaka (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/563,118

(22) PCT Filed: Mar. 1, 2017

(86) PCT No.: PCT/JP2017/008096
§ 371 (c)(1),
(2) Date: Sep. 29, 2017

(87) PCT Pub. No.: WO2017/163794
PCT Pub. Date: Sep. 28, 2017

(65) Prior Publication Data
US 2018/0079719 A1 Mar. 22, 2018

(30) Foreign Application Priority Data
Mar. 24, 2016 (JP) .................. 2016-059931

(51) Int. Cl.
| C08G 75/045 | (2016.01) |
| C08G 75/08 | (2006.01) |
| C07C 321/08 | (2006.01) |
| G02B 1/04 | (2006.01) |
| C07C 323/16 | (2006.01) |
| C08G 75/12 | (2016.01) |
| C07D 331/02 | (2006.01) |

(52) U.S. Cl.
CPC .......... *C07C 323/16* (2013.01); *C07C 321/08* (2013.01); *C08G 75/12* (2013.01); *G02B 1/041* (2013.01)

(58) Field of Classification Search
CPC .................................................... C08G 75/045
USPC ....................................................... 528/375
See application file for complete search history.

(56) References Cited

U.S. PATENT DOCUMENTS

| 5,084,545 A | 1/1992 | Nagata et al. |
| 5,807,975 A | 9/1998 | Amagai et al. |
| 6,117,923 A | 9/2000 | Amagai et al. |
| 6,531,532 B1 | 3/2003 | Yoshimura et al. |
| 2004/0254258 A1 | 12/2004 | Horikoshi et al. |
| 2007/0203318 A1 | 8/2007 | Kuma et al. |
| 2012/0142889 A1 | 6/2012 | Aoki et al. |
| 2012/0309932 A1 | 12/2012 | Takemura et al. |
| 2013/0231425 A1 | 9/2013 | Takemura et al. |
| 2015/0028270 A1 | 1/2015 | Tanaka et al. |
| 2015/0203633 A1 | 7/2015 | Takemura et al. |
| 2016/0202391 A1 | 7/2016 | Shimoda et al. |
| 2016/0259091 A1 | 9/2016 | Horita et al. |
| 2017/0051095 A1 | 2/2017 | Takemura et al. |

FOREIGN PATENT DOCUMENTS

| CN | 1930203 A | 3/2007 |
| EP | 2540762 | 1/2013 |
| EP | 2641928 | 9/2013 |
| EP | 2824129 | 1/2015 |
| JP | 09-110979 | 4/1997 |
| JP | 10-298287 | 11/1998 |
| JP | 2001-002783 | 1/2001 |
| JP | 2004-137481 | 5/2004 |
| KR | 1992-0010139 B1 | 2/1990 |
| KR | 2012-0031169 A | 3/2012 |
| WO | 2015/056665 | 4/2015 |
| WO | 2015/098718 | 7/2015 |
| WO | 2015/159811 | 10/2015 |

OTHER PUBLICATIONS

Extended European Search Report issued in Patent Application No. 17769839.6, dated Jan. 5, 2018.
International Search Report issued in WIPO Patent Application No. PCT/JP2017/008096, dated Apr. 11, 2017.
Written Opinion of the International Searching Authority in respect to International Application No. PCT/JP2017/008096, dated Apr. 11, 2017 , along with partial english translation thereof.

*Primary Examiner* — Duc Truong

(74) *Attorney, Agent, or Firm* — Greenblum & Bernstein, P.L.C.

(57) ABSTRACT

According to the present invention, it is possible to provide a polythiol composition, which comprises a polythiol (A) represented by formula (1) and a thiol compound (B) represented by formula (2).

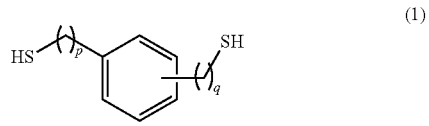

(1)

(In formula (1), p and q each independently represent an integer of 1 to 3.)

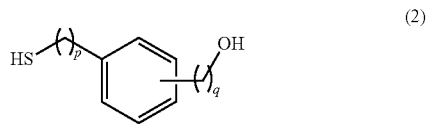

(2)

(In formula (2), p and q each independently represent an integer of 1 to 3.)

9 Claims, No Drawings

THIOL COMPOUND COMPOSITION FOR OPTICAL MATERIAL

TECHNICAL FIELD

The present invention relates to a composition for optical materials suitable for an optical material for a material plastic lens, a prism, an optical fiber, an information recording substrate, a filter or the like, in particular for a plastic lens, and the like.

BACKGROUND ART

For optical materials, in particular, for spectacle lenses, a method of using an episulfide compound is known from the viewpoint of physical properties (Patent Document 1). Further, as a method for further improving physical properties, for example, a composition in which a thiol compound is added to an episulfide compound for improving weather resistance (Patent Document 2) and a composition which consists of sulfur, episulfide and thiol for providing a higher refractive index (Patent Documents 3 and 4) have been proposed.

However, it is difficult to store such a thiol compound for a long period of time because of its high reactivity, and the purity is further reduced during long-term storage. There is a problem that white turbidity is caused in a composition containing such a thiol with a reduced purity when it is polymerized and cured. Because of intended use for optical materials, if white turbidity is caused after curing, all become defective products, resulting in a great loss. Accordingly, a technique of obtaining an optical material having excellent weather resistance, wherein the purity is not reduced during long-term storage, has been desired.

PRIOR ART DOCUMENTS

Patent Documents

Patent Document 1: Japanese Laid-Open Patent Publication No. H09-110979
Patent Document 2: Japanese Laid-Open Patent Publication No. H10-298287
Patent Document 3: Japanese Laid-Open Patent Publication No. 2001-2783
Patent Document 4: Japanese Laid-Open Patent Publication No. 2004-137481

SUMMARY OF THE INVENTION

Problems to be Solved by the Invention

The problem to be solved by the present invention is to provide a composition for optical materials, wherein a thiol compound can be stably stored, and by which an optical material having good transparency and weather resistance can be obtained.

Means for Solving the Problems

Under such circumstances, the present inventors diligently made researches and solved the problem by a composition for optical materials having a specific composition including polythiol and the like, and arrived at the present invention.

Specifically, the present invention is as described below.

[1] A polythiol composition, which comprises a polythiol (A) represented by formula (1):

$$HS{\leftarrow}_p\!\!\!\bigcirc\!\!\!{\rightarrow}_q SH \quad (1)$$

wherein p and q each independently represent an integer of 1 to 3; and a thiol compound (B) represented by formula (2):

$$HS{\leftarrow}_p\!\!\!\bigcirc\!\!\!{\rightarrow}_q OH \quad (2)$$

wherein p and q each independently represent an integer of 1 to 3.

[2] The polythiol composition according to item [1], wherein the ratio of the polythiol (A) is 93.0 to 99.999% by mass, and wherein the ratio of the thiol compound (B) is 0.001 to 7.0% by mass.

[3] The polythiol composition according to item [1] or [2], wherein the polythiol (A) is at least one selected from the group consisting of 1,2-bis(mercaptomethyl)benzene, 1,3-bis(mercaptomethyl)benzene and 1,4-bis(mercaptomethyl)benzene.

[4] A composition for optical materials, which comprises the polythiol composition according to any one of items [1] to [3] and a polymerizable compound (C).

[5] The composition for optical materials according to item [4], wherein the polymerizable compound (C) is a compound represented by formula (3):

$$\triangle\!\!\!-S{\leftarrow}_m\!\!-S{\rightarrow}_n\!\!-\triangle \quad (3)$$

wherein m represents an integer of 0 to 4 and n represents an integer of 0 to 2.

[6] The composition for optical materials according to item [4] or [5], wherein the ratio of the polymerizable compound (C) is 40 to 99.999% by mass.

[7] The composition for optical materials according to any one of items [4] to [6], wherein 0.0001 to 10 parts by mass of a polymerization catalyst is further added to 100 parts by mass of the composition for optical materials.

[8] A cured product obtained by curing the composition for optical materials according to item [7].

[9] An optical lens comprising the cured product according to item [8].

Advantageous Effect of the Invention

According to the composition of the present invention, it is possible to provide a composition for optical materials, wherein a thiol compound can be stably stored, and by which an optical material having good transparency and weather resistance can be obtained.

EMBODIMENTS FOR CARRYING OUT THE INVENTION

[Polythiol (A)]

The polythiol (A) to be used in the present invention is a compound represented by formula (1) below:

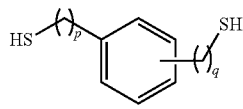

(1)

(In the formula, p and q each independently represent an integer of 1 to 3.)

From the viewpoint of weather resistance, preferred specific examples of the polythiol (A) include 1,2-bis(mercaptomethyl)benzene, 1,2-bis(mercaptoethyl)benzene, 1,3-bis(mercaptomethyl)benzene, 1,3-bis(mercaptoethyl)benzene, 1,4-bis(mercaptomethyl)benzene and 1,4-bis(mercaptoethyl)benzene. More preferred specific examples thereof include 1,2-bis(mercaptomethyl)benzene, 1,3-bis(mercaptomethyl)benzene and 1,4-bis(mercaptomethyl)benzene, and most preferred is 1,3-bis(mercaptomethyl)benzene. These substances may be used solely, or two or more of them may be used in combination. Further, commercially-available products thereof can be easily obtained.

[Thiol Compound (B)]

The thiol compound (B) to be used in the present invention is a compound represented by formula (2) below:

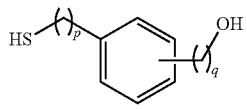

(2)

(In the formula, p and q each independently represent an integer of 1 to 3.)

In formula (2), p and q are each independently an integer of 1 to 3. Preferably, p and q are each independently an integer of 1 to 2. Most preferably, p and q are 1. Compounds represented by formula (2) may be used solely, or two or more of them may be used as a mixture.

Preferred specific examples of the thiol compound (B) include (2-(mercaptomethyl)phenyl)methanol, (3-(mercaptomethyl)phenyl)methanol, (4-(mercaptomethyl)phenyl)methanol, 2-(2-(2-mercaptoethyl)phenyl)ethane-1-ol, 2-(3-(2-mercaptoethyl)phenyl)ethane-1-01 and 2-(4-(2-mercaptoethyl)phenyl) ethane-1-ol. More preferred specific examples thereof include (2-(mercaptomethyl)phenyl)methanol, (3-(mercaptomethyl)phenyl)methanol and (4-(mercaptomethyl)phenyl)methanol, and most preferred is (3-(mercaptomethyl)phenyl)methanol.

The method for producing the thiol compound (B) is not particularly limited, and the compound can be suitably synthesized according to a publicly-known technique.

Examples of synthesis methods include a method in which a halogen compound is reacted with a thialation agent to obtain a compound represented by formula (4) below and then the obtained compound represented by formula (4) is reacted with an alkali to perform hydrolysis, thereby obtaining the compound represented by formula (2).

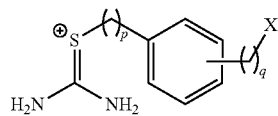

(4)

(In the formula, X represents a halogen atom, and p and q each independently represent an integer of 1 to 3.)

[Polythiol Composition]

The polythiol composition of the present invention comprises the polythiol (A) and the thiol compound (B).

The ratio of the polythiol (A) is preferably 93.0 to 99.999% by mass, and more preferably 97.0 to 99.95% by mass. Meanwhile, the ratio of the thiol compound (B) is preferably 0.001 to 7.0% by mass, and more preferably 0.005 to 3.0% by mass. When the ratios of these components are within the above-described ranges, storage stability of the polythiol composition can be improved.

The polythiol composition can be prepared, for example, by mixing predetermined amounts of the polythiol (A) and the thiol compound (B) homogeneously.

[Polymerizable Compound (C)]

The polymerizable compound (C) to be used in the present invention is a compound that can be polymerized, and specific examples thereof include an episulfide compound, a vinyl compound, a methacrylic compound, an acrylic compound and an allyl compound. From the viewpoint of optical characteristics, an episulfide compound is preferred, and a compound represented by formula (3) below is more preferred.

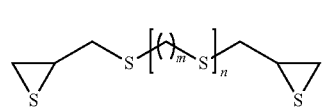

(3)

(In the formula, m represents an integer of 0 to 4, and n represents an integer of 0 to 2.)

Specific examples of the compound represented by formula (3) include episulfides such as bis($\beta$-epithiopropyl)sulfide, bis($\beta$-epithiopropyl)disulfide, bis($\beta$-epithiopropylthio)methane, 1,2-bis($\beta$-epithiopropylthio)ethane, 1,3-bis($\beta$-epithiopropylthio)propane and 1,4-bis($\beta$-epithiopropylthio)butane. Among the above-described compounds, bis($\beta$-epithiopropyl)sulfide (n=0 in formula (3)) and bis($\beta$-epithiopropyl)disulfide (m=0 and n=1 in formula (3)) are preferred, and bis($\beta$-epithiopropyl)sulfide (n=0 in formula (3)) is most preferred because it has excellent transparency. Compounds represented by formula (3) may be used solely, or two or more of them may be used as a mixture. These compounds can be synthesized according to a publicly-known technique, and for example, the method described in Japanese Laid-Open Patent Publication No. H09-110979 is known.

[Composition for Optical Materials]

The composition for optical materials of the present invention contains the aforementioned polythiol composition and the polymerizable compound (C).

The ratio of the polythiol composition in the composition for optical materials is preferably 0.001 to 60% by mass, and more preferably 2.0 to 40% by mass. Meanwhile, the ratio of the polymerizable compound (C) is preferably 40 to 99.999% by mass, and more preferably 60 to 98% by mass. When the ratios of these components are within the above-described ranges, transparency and weather resistance of cured products can be improved.

Further, the composition for optical materials of the present invention may include a polyisocyanate compound as a polymerizable compound for improving the strength of obtained resin. The content of the polyisocyanate compound is usually 1 to 25% by mass, preferably 2 to 25% by mass, and particularly preferably 5 to 20% by mass when the total amount of the composition for optical materials is 100% by mass. When the content of the polyisocyanate compound is less than 1% by mass, the strength may be reduced, and when the content is more than 25% by mass, the color tone may be deteriorated. As the polyisocyanate compound to be used in the present invention, compounds may be used solely, or two or more of them may be used as a mixture. Preferred compounds are isophorone diisocyanate, m-xylylene diisocyanate and 1,3-bis(isocyanatemethyl)cyclohexane.

The composition for optical materials of the present invention may include sulfur as a polymerizable compound for improving the refractive index of obtained resin. The content of sulfur is usually 0.1 to 15% by mass, preferably 0.2 to 10% by mass, and particularly preferably 0.3 to 5% by mass when the total amount of the composition for optical materials is 100% by mass.

When obtaining an optical material by polymerizing and curing the composition for optical materials of the present invention, it is preferred to add a polymerization catalyst. As the polymerization catalyst, amines, phosphines, onium salts, etc. may be used. Preferred polymerization catalysts are tetra-n-butylammonium bromide, triethylbenzyl ammonium chloride and tetra-n-butylphosphonium bromide.

Usually, the amount of the polymerization catalyst to be added is preferably 0.0001 to 10 parts by mass, more preferably 0.001 to 5.0 parts by mass, even more preferably 0.01 to 1.0 parts by mass, and most preferably 0.01 to 0.5 parts by mass when the total amount of the composition for optical materials prior to the addition of the polymerization catalyst is 100 parts by mass. When the amount of the polymerization catalyst to be added is more than 10 parts by mass, the composition may be rapidly polymerized. When the amount of the polymerization catalyst to be added is less than 0.0001 parts by mass, the composition for optical materials may be insufficiently cured, resulting in poor heat resistance.

Moreover, in the production of the optical material according to the production method of the present invention, it is surely possible to add additives such as an ultraviolet absorber, a blueing agent, a pigment and a polymerization modifier to the composition for optical materials to further improve practicability of the optical material obtained.

[Preparation Method and Curing Method for Composition for Optical Materials]

Specific amounts of the polythiol (A), the thiol compound (B), the polymerizable compound (C), and according to need, the polyisocyanate compound, sulfur, the polymerization catalyst and the additives are mixed homogeneously to prepare the composition for optical materials. It is preferred to remove impurities using, for example, a filter having a pore diameter of about 1 to 5 μm from the viewpoint of the quality of the optical material of the present invention.

The composition for optical materials of the present invention is usually polymerized as described below. Specifically, the curing time is usually 1 to 100 hours, and the curing temperature is usually −10° C. to 140° C. The polymerization is conducted by carrying out a step of retaining the composition at a predetermined polymerization temperature for a predetermined amount of time, a step of increasing the temperature at a rate of 0.1° C. to 100° C./h and a step of decreasing the temperature at a rate of 0.1° C. to 100° C./h, or a combination of these steps.

Further, it is preferred to anneal the obtained optical material at a temperature of 50 to 150° C. for about 10 minutes to 5 hours after curing is completed in terms of eliminating distortion of the optical material of the present invention. Moreover, the obtained optical material may be subjected to a surface treatment such as dyeing, hard coating, impact-resistant coating, antireflection treatment and imparting antifog properties according to need.

EXAMPLES

Hereinafter, the present invention will be described by way of working examples and comparative examples, but embodiments can be suitably changed within a range in which the effects of the present invention are exerted.

[Evaluation Methods]
[1. Stability]

Change in the purity of the thiol compound in the composition for optical materials was followed under nitrogen atmosphere at 60° C. for 1 week by GPC analysis (HPLC unit Prominence manufactured by Shimadzu Corporation). The case where the purity reduction is 0.1% or more and less than 1% was rated as "A". The case where the purity reduction is 1% or more and less than 3% was rated as "B". The case where the purity reduction is 3% or more and less than 5% was rated as "C". The case where the purity reduction is 5% or more and less than 10% was rated as "D". The case where the purity reduction is 10% or more and less than 15% was rated as "E". A, B, C and D are regarded as acceptable.

[2. Evaluation of Transparency of Optical Material]

According to methods described in the Examples and Comparative Examples below, 10 lenses of −4D were prepared, and the lenses were observed under a fluorescent light in a dark room. The case where no white turbidity was observed in the 10 lenses was rated as "A". The case where white turbidity was not observed in 7 to 9 lenses was rated as "B". The case where white turbidity was not observed in 6 lenses or less was rated as "C". A and B are regarded as acceptable.

[3. Evaluation of Weather Resistance of Optical Material (Color Tone Measurement)]
(1) Measurement of Initial Value A flat plate having a thickness of 3.0 mm was prepared, and the YI value was measured using a colorimeter JS-555 manufactured by Color Techno System Corporation. This value is "p".

(2) Measurement of Color Tone Change Caused by Light

After the initial value was measured, it was irradiated with carbon arc burning light for 60 hours, and after that, the YI value was measured. This value is "q". The value of (q−p)/p was calculated. The case where the value is less than 1.0 was rated as "A". The case where the value is 1.0 or more and less than 2.0 was rated as "B". The case where the value is 2.0 or more was rated as "C". A and B are regarded as acceptable.

Synthesis Example 1 (Synthesis of Thiol Compound (B))

In a 1 L four-neck reaction flask equipped with a stirring machine, a reflux cooling tube, a nitrogen gas purge tube and a thermometer, 24.7 g of 1,3-bis(chloromethyl)benzene, 5.3 g of thiourea and 90 g of water were mixed together, and the mixture was heated to reflux for 5 hours. The mixture was cooled to room temperature, and then 44.7 g of 50% aqueous solution of sodium hydroxide was added thereto under nitrogen atmosphere, and the mixture was heated to reflux for 2 hours. Next, the reaction solution was cooled to 40° C., hydrochloric acid was added thereto until pH became 2 to 3, and subsequently the mixture was stirred for 30 minutes to carry out neutralization. After the reaction was completed, extraction was carried out with 120 mL of toluene, and then toluene and a slight amount of water were removed under reduced pressure with heating. After that, water washing was carried out. The pressure was reduced with heating to remove water, and then filtration was carried out. After that, purification was carried out using a column, thereby obtaining 6.3 g of (3-(mercaptomethyl)phenyl)methanol (hereinafter referred to as "b1"). The identification data of the obtained compound is shown in Table 1 and formula (5).

TABLE 1

| | |
|---|---|
| $^1$H-NMR spectrum (DMSO-d6) | a; 5.27 ppm (1H) b; 4.61 ppm (2H) c; 3.73 ppm (1H) d; 7.51 ppm (1H) e; 3.73 ppm (1H) f; 7.19 ppm (1H) g; 3.82 ppm (2H) h; 1.7 ppm (1H) |
| $^{13}$C-NMR spectrum (DMSO-d6) | 1; 65 ppm 2; 141.2 ppm 3; 125.5 ppm 4; 128.9 ppm 5; 126.6 ppm 6; 139.8 ppm 7; 127.7 ppm 8; 28.3 ppm |
| MS spectrum (ESI method) | [M + H]$^+$ = 154.05 |

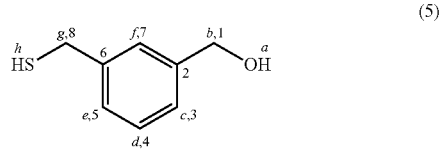

(5)

Synthesis Example 2 (Synthesis of Thiol Compound (B))

In a 1 L four-neck reaction flask equipped with a stirring machine, a reflux cooling tube, a nitrogen gas purge tube and a thermometer, 28.4 g of 1,4-bis(2-chloroethyl)benzene, 5.3 g of thiourea and 90 g of water were mixed together, and the mixture was heated to reflux for 5 hours. The mixture was cooled to room temperature, and then 44.7 g of 50% aqueous solution of sodium hydroxide was added thereto under nitrogen atmosphere, and the mixture was heated to reflux for 2 hours. Next, the reaction solution was cooled to 40° C., hydrochloric acid was added thereto until pH became 2 to 3, and subsequently the mixture was stirred for 30 minutes to carry out neutralization. After the reaction was completed, extraction was carried out with 120 mL of toluene, and then toluene and a slight amount of water were removed under reduced pressure with heating. After that, water washing was carried out. The pressure was reduced with heating to remove water, and then filtration was carried out. After that, purification was carried out using a column, thereby obtaining 5.1 g of 2-(4-(2-mercaptoethyl)phenyl)ethane-1-ol (hereinafter referred to as "b2"). The identification data of the obtained compound is shown in Table 2 and formula (6).

TABLE 2

| | |
|---|---|
| $^1$H-NMR spectrum (DMSO-d6) | a; 4.58 ppm (1H) b; 3.63 ppm (2H) c; 2.87 ppm (2H) d; 7.05 ppm (1H) e; 7.05 ppm (1H) f; 7.05 ppm (1H) g; 7.05 ppm (1H) h; 2.85 ppm (2H) i; 2.89 ppm (2H) j; 1.4 ppm (1H) |
| $^{13}$C-NMR spectrum (DMSO-d6) | 1; 61.1 ppm 2; 38.9 ppm 3; 135.4 ppm 4; 127.6 ppm 5; 127.6 ppm 6; 137.6 ppm 7; 127.6 ppm 8; 127.6 ppm 9; 40.4 ppm 10; 28.0 ppm |
| MS spectrum (ESI method) | [M + H]$^+$ = 182.08 |

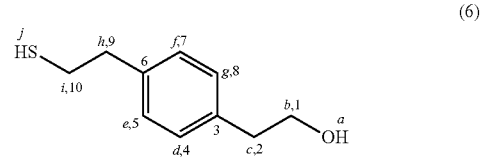 [SMILES: OCCc1ccc(CCS)cc1]

(6)

Examples 1-7

To 1,3-bis(mercaptomethyl)benzene (hereinafter referred to as "a1"), (3-(mercaptomethyl)phenyl)methanol (b1) was added in an amount shown in Table 3 to evaluate stability. The results are shown in Table 3.

Examples 8-14

To 1,4-bis(2-mercaptoethyl)benzene (hereinafter referred to as "a2"), 2-(4-(2-mercaptoethyl)phenyl)ethane-1-ol (b2) was added in an amount shown in Table 3 to evaluate stability. The results are shown in Table 3.

Comparative Example 1

The stability of only a1 was evaluated. The results are shown in Table 3.

Comparative Example 2

The stability of only a2 was evaluated. The results are shown in Table 3.

TABLE 3

| | Polythiol (A) (parts by mass) | Thiol (B) (parts by mass) | Stability |
|---|---|---|---|
| Example 1 | a1 (99.999) | b1 (0.001) | C |
| Example 2 | a1 (99.995) | b1 (0.005) | B |
| Example 3 | a1 (99.99) | b1 (0.01) | A |
| Example 4 | a1 (99) | b1 (1.0) | A |
| Example 5 | a1 (97) | b1 (3.0) | B |
| Example 6 | a1 (95) | b1 (5.0) | C |
| Example 7 | a1 (93) | b1 (7.0) | D |
| Comparative Example 1 | a1 (100) | Absent | E |
| Example 8 | a2 (99.999) | b2 (0.001) | C |
| Example 9 | a2 (99.995) | b2 (0.005) | B |
| Example 10 | a2 (99.99) | b2 (0.01) | A |
| Example 11 | a2 (99) | b2 (1.0) | A |
| Example 12 | a2 (97) | b2 (3.0) | B |
| Example 13 | a2 (95) | b2 (5.0) | C |
| Example 14 | a2 (93) | b2 (7.0) | D |
| Comparative Example 2 | a2 (100) | Absent | E |

Examples 15-21

With a1, b1 was mixed in an amount shown in Table 4 to prepare a composition, and it was stored under nitrogen atmosphere at 60° C. for 1 week. To 7 parts by mass of the composition, 93 parts by mass of bis(β-epithiopropyl)sulfide (hereinafter referred to as "c1") as the polymerizable compound (C), 1.0 parts by mass of 2-(2-hydroxy-5-t-octylphenyl)-2H-benzotriazol as an ultraviolet absorber and 0.05 parts by mass of tetra-n-butylphosphonium bromide as a polymerization catalyst were added, and after that, the mixture was well mixed homogeneously at 20° C.

Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was heated at 30° C. for 10 hours, then the temperature was elevated to 100° C. over 10 hours at a constant rate, and finally, it was heated at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The color tone and the weather resistance of the flat plate were evaluated, and the results thereof are shown in Table 4 together with the results regarding transparency of the −4D lens.

Comparative Example 3

To 93 parts by mass of c1, 7 parts by mass of a1 stored under nitrogen atmosphere at 60° C. for 1 week, 1.0 parts by mass of 2-(2-hydroxy-5-t-octylphenyl)-2H-benzotriazol as an ultraviolet absorber and 0.05 parts by mass of tetra-n-butylphosphonium bromide as a polymerization catalyst were added, and after that, the mixture was well mixed homogeneously at 20° C. Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was heated at 30° C. for 10 hours, then the temperature was elevated to 100° C. over 10 hours at a constant rate, and finally, it was heated at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The color tone and the weather resistance of the flat plate were evaluated, and the results thereof are shown in Table 4 together with the results regarding transparency of the −4D lens.

Examples 22-28

With a2, b2 was mixed in an amount shown in Table 4 to prepare a composition, and it was stored under nitrogen atmosphere at 60° C. for 1 week. To 7 parts by mass of the composition, 93 parts by mass of c1, 1.0 parts by mass of 2-(2-hydroxy-5-t-octylphenyl)-2H-benzotriazol as an ultraviolet absorber and 0.05 parts by mass of tetra-n-butylphosphonium bromide as a polymerization catalyst were added, and after that, the mixture was well mixed homogeneously at 20° C. Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was heated at 30° C. for 10 hours, then the temperature was elevated to 100° C. over 10 hours at a constant rate, and finally, it was heated at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The color tone and the weather resistance of the flat plate were evaluated, and the results thereof are shown in Table 4 together with the results regarding transparency of the −4D lens.

Comparative Example 4

To 93 parts by mass of c1, 7 parts by mass of a2 stored under nitrogen atmosphere at 60° C. for 1 week, 1.0 parts by mass of 2-(2-hydroxy-5-t-octylphenyl)-2H-benzotriazol as an ultraviolet absorber and 0.05 parts by mass of tetra-n-butylphosphonium bromide as a polymerization catalyst were added, and after that, the mixture was well mixed homogeneously at 20° C. Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was heated at 30° C. for 10 hours, then the temperature was elevated to 100° C. over 10 hours at a constant rate, and finally, it was heated at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The color tone and the weather resistance of the flat plate were evaluated, and the results thereof are shown in Table 4 together with the results regarding transparency of the −4D lens.

Examples 29-35

With a1, b1 was mixed in an amount shown in Table 4 to prepare a composition, and it was stored under nitrogen atmosphere at 60° C. for 1 week. To 7 parts by mass of the composition, 93 parts by mass of bis(β-epithiopropyl)disulfide (hereinafter referred to as "c2") as the polymerizable compound (C), 1.0 parts by mass of 2-(2-hydroxy-5-t-octylphenyl)-2H-benzotriazol as an ultraviolet absorber and 0.05 parts by mass of tetra-n-butylphosphonium bromide as a polymerization catalyst were added, and after that, the mixture was well mixed homogeneously at 20° C.

Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was heated at 30° C. for 10 hours, then the temperature was elevated to 100° C. over 10 hours at a constant rate, and finally, it was heated at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The color tone and the weather resistance of the flat plate were evaluated, and the results thereof are shown in Table 4 together with the results regarding transparency of the −4D lens.

Comparative Example 5

To 93 parts by mass of c2, 7 parts by mass of a1 stored under nitrogen atmosphere at 60° C. for 1 week, 1.0 parts by mass of 2-(2-hydroxy-5-t-octylphenyl)-2H-benzotriazol as an ultraviolet absorber and 0.05 parts by mass of tetra-n- butylphosphonium bromide as a polymerization catalyst were added, and after that, the mixture was well mixed homogeneously at 20° C. Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was heated at 30° C. for 10 hours, then the temperature was elevated to 100° C. over 10 hours at a constant rate, and finally, it was heated at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The color tone and the weather resistance of the flat plate were evaluated, and the results thereof are shown in Table 4 together with the results regarding transparency of the −4D lens.

Examples 36-42

With a2, b2 was mixed in an amount shown in Table 4 to prepare a composition, and it was stored under nitrogen atmosphere at 60° C. for 1 week. To 7 parts by mass of the composition, 93 parts by mass of c2, 1.0 parts by mass of 2-(2-hydroxy-5-t-octylphenyl)-2H-benzotriazol as an ultraviolet absorber and 0.05 parts by mass of tetra-n-butylphosphonium bromide as a polymerization catalyst were added, and after that, the mixture was well mixed homogeneously at 20° C. Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was heated at 30° C. for 10 hours, then the temperature was elevated to 100° C. over 10 hours at a constant rate, and finally, it was heated at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The color tone and the weather resistance of the flat plate were evaluated, and the results thereof are shown in Table 4 together with the results regarding transparency of the −4D lens.

Comparative Example 6

To 93 parts by mass of c2, 7 parts by mass of a2 stored under nitrogen atmosphere at 60° C. for 1 week, 1.0 parts by mass of 2-(2-hydroxy-5-t-octylphenyl)-2H-benzotriazol as an ultraviolet absorber and 0.05 parts by mass of tetra-n-butylphosphonium bromide as a polymerization catalyst were added, and after that, the mixture was well mixed homogeneously at 20° C. Next, the obtained mixture was subjected to the deaeration treatment at a vacuum degree of 1.3 kPa. It was injected into a mold composed of two glass plates and a tape (for a flat plate having a thickness of 3.0 mm and a −4D lens), and it was heated at 30° C. for 10 hours, then the temperature was elevated to 100° C. over 10 hours at a constant rate, and finally, it was heated at 100° C. for 1 hour to be polymerized and cured. After cooling, the obtained product was released from the mold and annealed at 110° C. for 60 minutes, thereby obtaining a molded plate (a flat plate having a thickness of 3.0 mm and a −4D lens). The color tone and the weather resistance of the flat plate were evaluated, and the results thereof are shown in Table 4 together with the results regarding transparency of the −4D lens.

TABLE 4

| | Composition in polythiol composition (% by mass) | | Composition for optical materials (parts by mass) | | | |
|---|---|---|---|---|---|---|
| | Polythiol (A) | Thiol (B) | Polythiol composition | Polymerizable compound (C) | Transparency | Weather resistance |
| Example 15 | a1 (99.999) | b1 (0.001) | 7 | c1 (93) | B | B |
| Example 16 | a1 (99.995) | b1 (0.005) | 7 | c1 (93) | B | A |
| Example 17 | a1 (99.990) | b1 (0.01) | 7 | c1 (93) | A | A |
| Example 18 | a1 (99) | b1 (1.0) | 7 | c1 (93) | A | A |
| Example 19 | a1 (97) | b1 (3.0) | 7 | c1 (93) | B | A |
| Example 20 | a1 (95) | b1 (5.0) | 7 | c1 (93) | B | A |
| Example 21 | a1 (93) | b1 (7.0) | 7 | c1 (93) | B | C |
| Comparative Example 3 | a1 (100) | Absent | 7 | c1 (93) | C | C |
| Example 22 | a2 (99.999) | b2 (0.001) | 7 | c1 (93) | B | B |
| Example 23 | a2 (99.995) | b2 (0.005) | 7 | c1 (93) | B | B |
| Example 24 | a2 (99.990) | b2 (0.01) | 7 | c1 (93) | A | A |
| Example 25 | a2 (99) | b2 (1.0) | 7 | c1 (93) | A | A |
| Example 26 | a2 (97) | b2 (3.0) | 7 | c1 (93) | B | A |
| Example 27 | a2 (95) | b2 (5.0) | 7 | c1 (93) | B | A |
| Example 28 | a2 (93) | b2 (7.0) | 7 | c1 (93) | B | C |
| Comparative Example 4 | a2 (100) | Absent | 7 | c1 (93) | C | C |
| Example 29 | a1 (99.999) | b1 (0.001) | 7 | c2 (93) | B | B |
| Example 30 | a1 (99.995) | b1 (0.005) | 7 | c2 (93) | B | A |
| Example 31 | a1 (99.990) | b1 (0.01) | 7 | c2 (93) | B | A |
| Example 32 | a1 (99) | b1 (1.0) | 7 | c2 (93) | A | A |
| Example 33 | a1 (97) | b1 (3.0) | 7 | c2 (93) | B | A |
| Example 34 | a1 (95) | b1 (5.0) | 7 | c2 (93) | B | A |
| Example 35 | a1 (93) | b1 (7.0) | 7 | c2 (93) | B | C |
| Comparative Example 5 | a1 (100) | Absent | 7 | c2 (93) | C | C |
| Example 36 | a2 (99.999) | b2 (0.001) | 7 | c2 (93) | B | B |
| Example 37 | a2 (99.995) | b2 (0.005) | 7 | c2 (93) | B | B |

TABLE 4-continued

| | Composition in polythiol composition (% by mass) | | Composition for optical materials (parts by mass) | | | |
|---|---|---|---|---|---|---|
| | Polythiol (A) | Thiol (B) | Polythiol composition | Polymerizable compound (C) | Transparency | Weather resistance |
| Example 38 | a2 (99.990) | b2 (0.01) | 7 | c2 (93) | A | A |
| Example 39 | a2 (99) | b2 (1.0) | 7 | c2 (93) | B | A |
| Example 40 | a2 (97) | b2 (3.0) | 7 | c2 (93) | B | A |
| Example 41 | a2 (95) | b2 (5.0) | 7 | c2 (93) | B | A |
| Example 42 | a2 (93) | b2 (7.0) | 7 | c2 (93) | B | C |
| Comparative Example 6 | a2 (100) | Absent | 7 | c2 (93) | C | C |

The invention claimed is:

1. A polythiol composition, which comprises a polythiol (A) represented by formula (1):

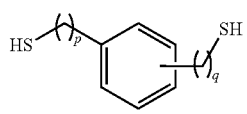
(1)

wherein p and q each independently represent an integer of 1 to 3; and a thiol compound (B) represented by formula (2):

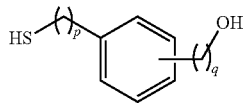
(2)

wherein p and q each independently represent an integer of 1 to 3.

2. The polythiol composition according to claim 1, wherein the ratio of the polythiol (A) is 93.0 to 99.999% by mass, and wherein the ratio of the thiol compound (B) is 0.001 to 7.0% by mass.

3. The polythiol composition according to claim 1, wherein the polythiol (A) is at least one selected from the group consisting of 1,2-bis(mercaptomethyl)benzene, 1,3-bis(mercaptomethyl)benzene and 1,4-bis(mercaptomethyl)benzene.

4. A composition for optical materials, which comprises the polythiol composition according to claim 1 and a polymerizable compound (C).

5. The composition for optical materials according to claim 4, wherein the polymerizable compound (C) is a compound represented by formula (3):

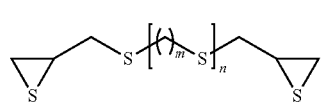
(3)

wherein m represents an integer of 0 to 4 and n represents an integer of 0 to 2.

6. The composition for optical materials according to claim 4, wherein the ratio of the polymerizable compound (C) is 40 to 99.999% by mass.

7. The composition for optical materials according to claim 4, wherein 0.0001 to 10 parts by mass of a polymerization catalyst is further added to 100 parts by mass of the composition for optical materials.

8. A cured product obtained by curing the composition for optical materials according to claim 7.

9. An optical lens comprising the cured product according to claim 8.

* * * * *